United States Patent
Park et al.

(10) Patent No.: US 10,082,453 B2
(45) Date of Patent: Sep. 25, 2018

(54) AIRBORNE MICROBIAL MEASUREMENT APPARATUS AND MEASUREMENT METHOD THEREOF

(71) Applicants: LG ELECTRONICS INC., Seoul (KR); NATIONAL UNIVERSITY CORPORATION TOYOHASHI UNIVERSITY OF TECHNOLOGY, Toyohashi, Aichi (JP)

(72) Inventors: Chulwoo Park, Seoul (KR); Sunghwa Lee, Seoul (KR); Akira Mizuno, Toyohashi (JP); Kazunori Takashima, Toyohashi (JP); Hirofumi Kurita, Toyohashi (JP); Hachiro Yasuda, Toyohashi (JP)

(73) Assignees: LG ELECTRONICS INC., Seoul (KR); NATIONAL UNIVERSITY CORPORATION TOYOHASHI UNIVERSITY OF TECHNOLOGY, Aichi (JP)

( * ) Notice: Subject to any disclaimer, the term of this patent is extended or adjusted under 35 U.S.C. 154(b) by 0 days.

(21) Appl. No.: 15/122,055

(22) PCT Filed: Sep. 19, 2014

(86) PCT No.: PCT/KR2014/008759
§ 371 (c)(1),
(2) Date: Aug. 26, 2016

(87) PCT Pub. No.: WO2015/129979
PCT Pub. Date: Sep. 3, 2015

(65) Prior Publication Data
US 2017/0016811 A1    Jan. 19, 2017

(30) Foreign Application Priority Data
Feb. 27, 2014  (KR) .................. 10-2014-0023206

(51) Int. Cl.
*G01N 15/06* (2006.01)
*G01N 21/76* (2006.01)
(Continued)

(52) U.S. Cl.
CPC .......... *G01N 15/0606* (2013.01); *C12Q 1/04* (2013.01); *G01N 21/76* (2013.01);
(Continued)

(58) Field of Classification Search
None
See application file for complete search history.

(56) References Cited

U.S. PATENT DOCUMENTS

| 5,989,824 A | 11/1999 | Birmingham et al. |
| 6,043,066 A | 3/2000 | Mangano et al. |

(Continued)

FOREIGN PATENT DOCUMENTS

| CN | 101715557 A | 5/2010 |
| EP | 2 169 403 A1 | 3/2010 |

(Continued)

OTHER PUBLICATIONS

Masudur Rahman et al., "Fundamental study on quasi-real-time detection of airborne bio-particles using discharge plasma", ScienceDirect, Thin Solid Films 516 (2008), pp. 6699-6703, XP022763660.

*Primary Examiner* — Betty J Forman
(74) *Attorney, Agent, or Firm* — Dentons US LLP

(57) ABSTRACT

An airborne microbial measurement apparatus and a measurement method thereof are provided. An airborne microbial measurement apparatus according to an embodiment includes a discharge apparatus including a discharge electrode and a voltage supply unit applying a high voltage to the discharge electrode. A substrate is provided to a side of the discharge apparatus to collect an airborne microbe from air (Continued)

by a high voltage applied to the discharge electrode. A reagent injection apparatus supplies a dyeing reagent to the microbe collected on the substrate or a DNA of the microbe. A light emission measurement apparatus senses a quantity of light generated from the DNA to which the dyeing reagent is supplied. The discharge apparatus includes a controller controlling the voltage supply unit so that the voltage is applied to collect the airborne microbe or destroy an external wall of the collected airborne microbe.

5 Claims, 3 Drawing Sheets

(51) Int. Cl.
*C12Q 1/04* (2006.01)
*G01N 21/84* (2006.01)
*G01N 15/00* (2006.01)
*G01N 21/64* (2006.01)

(52) U.S. Cl.
CPC ..... *G01N 15/0637* (2013.01); *G01N 21/6428* (2013.01); *G01N 21/8483* (2013.01); *G01N 2015/0069* (2013.01); *G01N 2021/6439* (2013.01)

(56) References Cited

U.S. PATENT DOCUMENTS

| | | | |
|---|---|---|---|
| 6,403,367 | B1 | 6/2002 | Cheng et al. |
| 6,498,497 | B1 | 12/2002 | Chow et al. |
| 2003/0215845 | A1 | 11/2003 | Bille |
| 2008/0187946 | A1 | 8/2008 | Hwang et al. |
| 2009/0010801 | A1 | 1/2009 | Murphy et al. |
| 2010/0089754 | A1* | 4/2010 | Mizuno ............... C12Q 1/6825 204/461 |
| 2012/0190040 | A1 | 7/2012 | Talebpour et al. |
| 2014/0017723 | A1 | 1/2014 | Hwang et al. |

FOREIGN PATENT DOCUMENTS

| | | |
|---|---|---|
| JP | 2001-157598 A | 6/2001 |
| JP | 2012-132695 A | 7/2012 |
| KR | 10-1070222 B1 | 10/2011 |
| KR | 10-2012-0086384 A | 8/2012 |
| KR | 10-2013-0004626 A | 1/2013 |
| WO | 2008/156135 A1 | 12/2008 |

* cited by examiner

[Fig. 1]
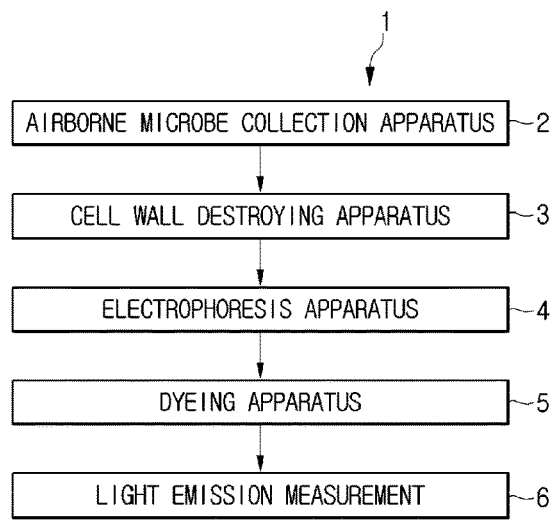
[Fig. 2]
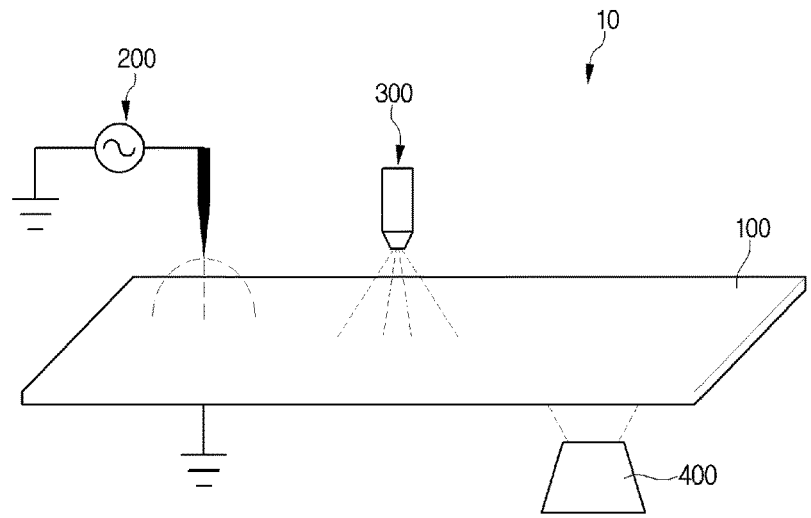
[Fig. 3]
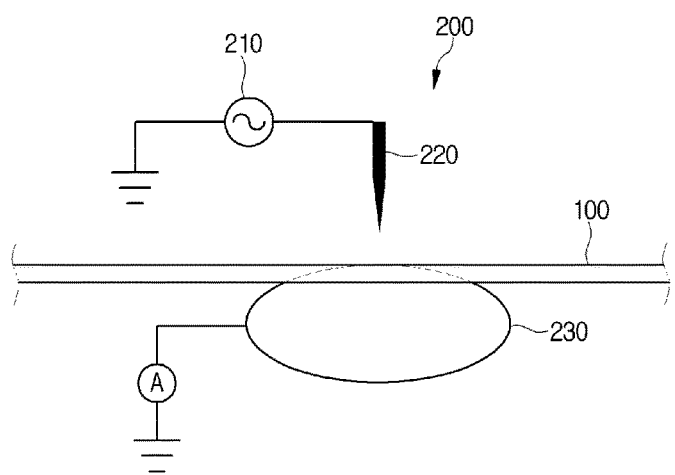

[Fig. 4]
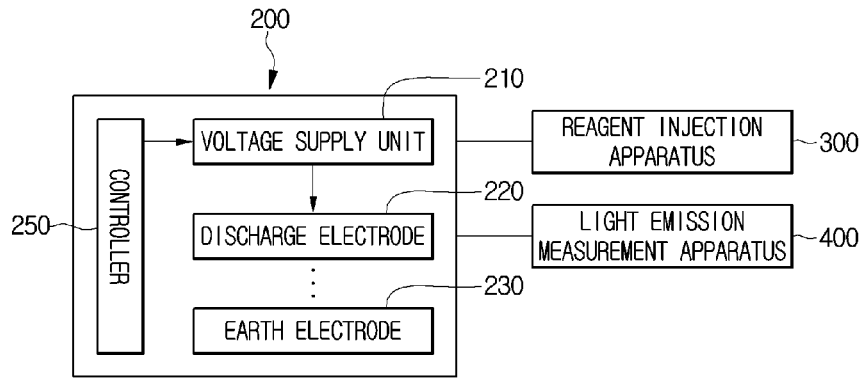
[Fig. 5]
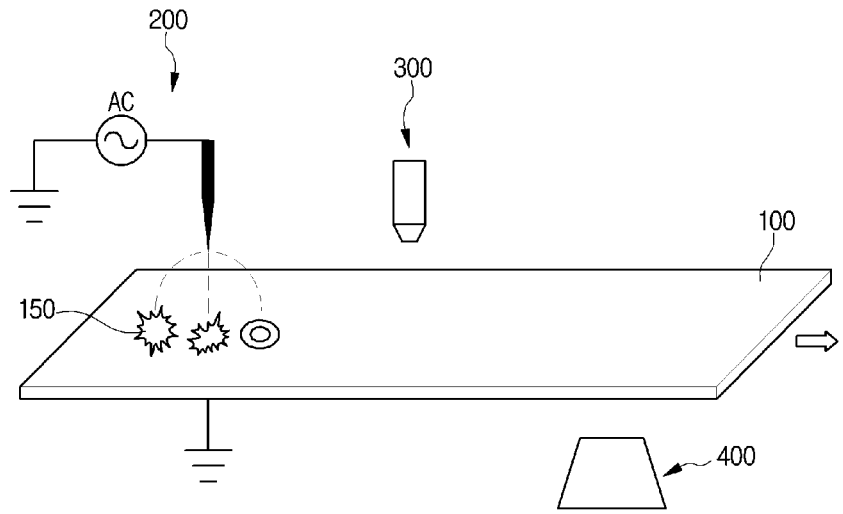
[Fig. 6]
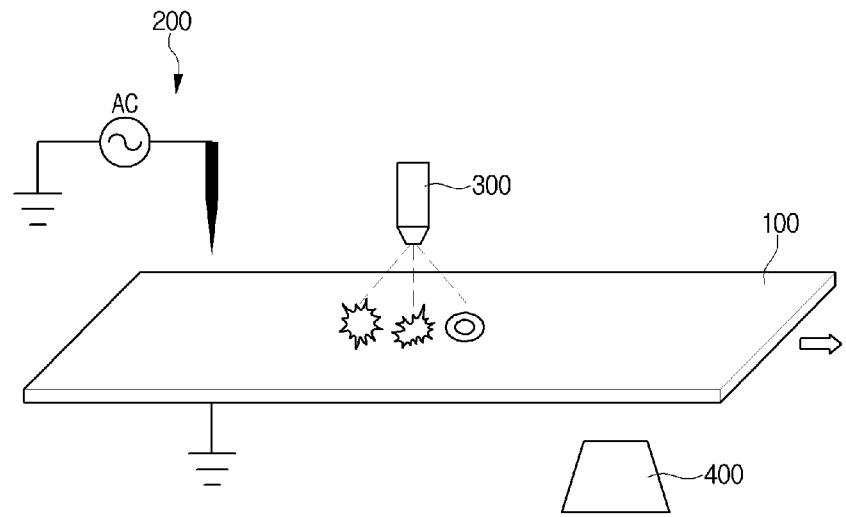

[Fig. 7]
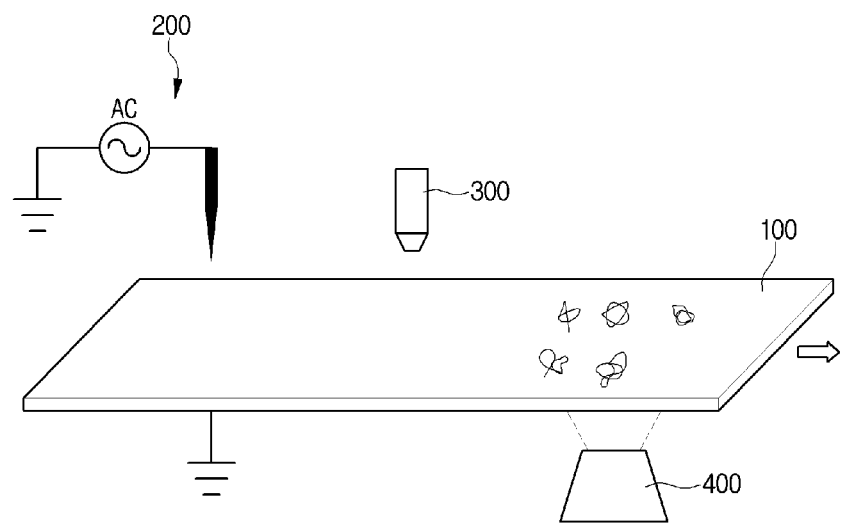
[Fig. 8]
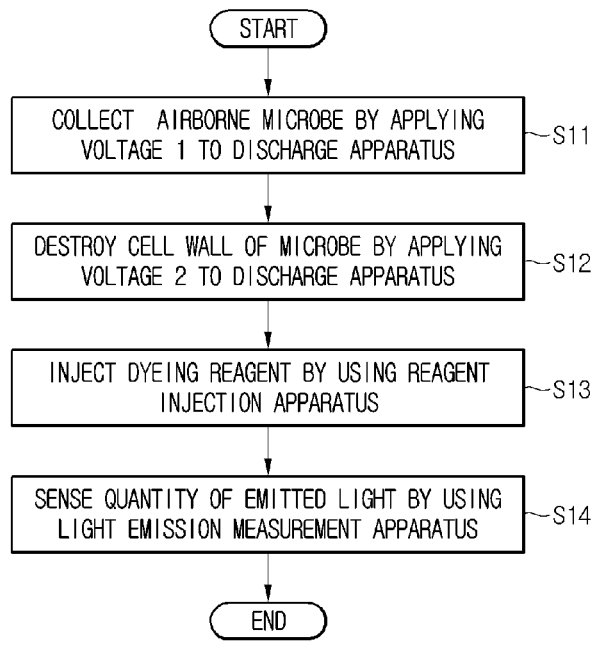

AIRBORNE MICROBIAL MEASUREMENT APPARATUS AND MEASUREMENT METHOD THEREOF

This application is a National Stage Application of International Application No. PCT/KR2014/008759, filed on Sep. 19, 2014, which claims the benefit of Korean Patent Application No. 10-2014-0023206, filed on Feb. 27, 2014, all of which are hereby incorporated by reference in their entirety for all purposes as if fully set forth herein.

TECHNICAL FIELD

The present disclosure relates to an airborne microbial measurement apparatus and a measurement method thereof.

BACKGROUND ART

Recently, avian influenza and new influenza have been at issue, and thus airborne infection has been on the rise. Therefore, measurement of airborne microbes from air has been more significantly handled, and accordingly, a biosensor market has grown by a great deal.

Examples of a typical method of measuring airborne microbes from air include a cultivation method of collecting airborne organism particles of a sample gas on a surface of a solid or a liquid suitable for proliferation, performing cultivation under an environment of appropriate temperature and humidity for a predetermined period, and obtaining the number of collected microbes from the number of colonies exhibited on the surface, and a dyeing method of using a fluorescence microscope after dyeing.

Currently, it is possible to perform a rapid operation by reducing a time of a series of processes required in ATP removing treatment, ATP extraction, and measurement of the quantity of emitted light to about 30 minutes by an ATP bioluminescence detection method using a principle that ATP (adenosine triphosphate) and luciferin/luciferase are reacted to emit light.

FIG. 1 shows a constitution of a typical airborne microbial measurement apparatus.

Referring to FIG. 1, a typical airborne microbial measurement apparatus 1 includes an airborne microbe collection apparatus 2 collecting airborne microbes that are present in air, a cell wall destroying apparatus 3 destroying cell walls of the microbes collected in the airborne microbe collection apparatus 2 to extract DNAs, an electrophoresis apparatus 4 separating the extracted DNAs, a dyeing apparatus 5 dyeing the separated DNAs, and a light emission measurement apparatus measuring the intensity of light emitted from the dyed DNAs.

The airborne microbe collection apparatus 2 or the cell wall destroying apparatus 3 may be constituted so that a voltage is applied to the airborne microbes by using a discharge electrode.

In addition, the electrophoresis apparatus 4 includes a membrane (substrate) coated with an agarose gel, and the DNA having a predetermined polarity may pass through a gel layer and be attached to the membrane having an opposite polarity.

As described above, the typical airborne microbial measurement apparatus 1 has a limitation in that since a plurality of apparatuses are complicatedly constituted to be continuously operated, a measurement method is cumbersome and a measurement time may be delayed.

In addition, there is a disadvantage in that since the membrane (substrate) coated with the agarose gel needs to be replaced after used once, a cost is high and an operation is cumbersome.

DISCLOSURE OF INVENTION

Technical Problem

Embodiments provide an airborne microbial measurement apparatus and a measurement method thereof, in which an airborne microbe that is present in the air is rapidly measured.

Solution to Problem

In one embodiment, an airborne microbial measurement apparatus includes: a discharge apparatus including a discharge electrode and a voltage supply unit applying a high voltage to the discharge electrode; a substrate provided to a side of the discharge apparatus to collect an airborne microbe from air by the high voltage applied to the discharge electrode; a reagent injection apparatus supplying a dyeing reagent to the microbe collected on the substrate or a DNA of the microbe; and a light emission measurement apparatus sensing a quantity of light generated from the DNA to which the dyeing reagent is supplied, in which the discharge apparatus includes a controller controlling the voltage supply unit so that the voltage is applied to collect the airborne microbe or destroy an external wall of the collected airborne microbe.

Also, the controller may control the voltage supply unit so that voltage 1 is applied to collect the airborne microbe from air on the substrate, and when the microbe is collected on the substrate, the controller may control the voltage supply unit so that voltage 2 is applied to destroy the external wall of the collected microbe.

Also, the voltage 2 may be higher than the voltage 1.

Also, the controller may control the voltage supply unit so that a level of the voltage 2 applied to destroy the external wall of the microbe is changed according to a type of the microbe.

Also, the controller may control the voltage supply unit so that the level of the voltage 2 is sequentially increased.

Also, an airborne microbe may include viruses, bacteria, and molds, and the controller may control the voltage supply unit so that the level of the voltage 2 is increased to sequentially destroy protein shells of the viruses, cell walls of the bacteria, and cell walls of the molds.

Also, the substrate may include a plastic material having polyethylene and polypropylene mixed therein.

Also, the light emission measurement apparatus may include a blue LED and a CCD camera.

In another embodiment, an airborne microbial measurement method includes: collecting an airborne microbe on a substrate by applying a voltage to a discharge apparatus; destroying an external wall of the microbe collected on the substrate and extracting a DNA by applying the voltage to the discharge apparatus; injecting a dyeing reagent to the extracted DNA to perform light emission or fluorescence; and sensing a quantity of emitted or fluorescent light by using a light emission measurement apparatus.

Also, the collecting of the airborne microbe on the substrate may include applying the voltage 1 to the discharge apparatus, and the destroying of the external wall of the microbe collected on the substrate and the extracting of the DNA may include applying the voltage 2 to the discharge apparatus.

Also, the voltage 2 may be higher than the voltage 1.

Also, the voltage 2 may form voltages having different levels according to a type of the microbe.

Also, the destroying of the external wall of the microbe collected on the substrate and the extracting of the DNA may include sequentially increasing the voltage 2 to sequentially destroy external walls of a plurality of microbes from the microbe having a weak external wall to the microbe having a strong external wall.

The details of one or more embodiments are set forth in the accompanying drawings and the description below. Other features will be apparent from the description and drawings, and from the claims.

Advantageous Effects of Invention

According to an airborne microbial measurement apparatus and a measurement method thereof according to embodiments, there are effects in that a microbe collecting apparatus and a cell wall destroying apparatus are not separately required, and collection of a microbe and destroying of a cell wall or a protein shell of the microbe are sequentially performed by using one discharge apparatus, and thus the measurement apparatus becomes compact, and the measurement method is simple.

In addition, there is an effect in that levels of voltages applied to a discharge electrode are sequentially increased to sequentially destroy external walls of viruses, bacteria, and molds and thus extract a DNA, thereby measuring a concentration of the microbe for each type.

Furthermore, there are merits in that since a film unit on which the microbe is collected is made of a plastic material, the film unit is easily washed and used over a relatively long period of time.

Also, there is an effect in that since a low-priced light emission measurement apparatus is used, a manufacturing cost of the measurement apparatus is reduced.

BRIEF DESCRIPTION OF DRAWINGS

FIG. 1 is a block diagram showing a constitution of a typical airborne microbial measurement apparatus.

FIG. 2 is a view showing a constitution of an airborne microbial measurement apparatus according to an embodiment.

FIG. 3 is a view showing a constitution of a discharge apparatus according to the embodiment.

FIG. 4 is a block diagram showing a constitution of the airborne microbial measurement apparatus according to the embodiment.

FIGS. 5 to 7 are views showing an airborne microbial measurement process according to the embodiment.

FIG. 8 is a flowchart showing an airborne microbial measurement method according to the embodiment.

BEST MODE FOR CARRYING OUT THE INVENTION

Hereinafter, specific embodiments will be described with reference to the drawings. However, the spirit of the present disclosure is not limited to the proposed embodiments, and a person with ordinary skill in the art understanding the spirit of the present disclosure may easily propose another embodiment within the same scope.

FIG. 2 is a view showing a constitution of an airborne microbial measurement apparatus according to an embodiment, and FIG. 3 is a view showing a constitution of a discharge apparatus according to the embodiment.

Referring to FIGS. 2 and 3, an airborne microbial measurement apparatus 10 according to the embodiment includes a film unit 100 as "a substrate" on which an airborne microbe is collected from air, and a discharge apparatus 200 applying a high voltage to collect the airborne microbe on the film unit 100.

The film unit 100 is constituted by a plastic material. For example, the film unit 100 is formed of a plastic material having polyethylene and polypropylene mixed therein.

The discharge apparatus 200 includes an AC corona discharge apparatus using plasma discharge.

In detail, the discharge apparatus 200 includes a voltage supply unit 210 applying the high voltage, a needle-shaped discharge electrode 220 forming a strong electric field due to the high voltage applied from the voltage supply unit 210, and an earth electrode 230 disposed to be spaced apart from the discharge electrode 220. The earth electrode 230 may have a flat plate shape and be positioned on a lower side of the film unit 100.

When the high voltage is applied from the voltage supply unit 210 to form the strong electric field on the discharge unit 220, corona discharge may occur due to a difference in voltage of the discharge electrode 220 and the earth electrode 230.

In addition, anions (−) or cations (+) generated during corona discharge may be electrified with the airborne microbe, and thus the airborne microbe may be electrically charged. The electrically charged airborne microbe may be collected on or attached to a surface of the film unit 100.

The discharge apparatus 200 may be operated so that an external wall of the microbe collected on the film unit 100, that is, a cell wall or a protein shell, is destroyed. That is, the discharge apparatus 200 may function as "a destroying apparatus" destroying the cell wall or the protein shell of the microbe.

When the discharge apparatus 200 functions as the destroying apparatus to destroy the external wall of the microbe, a DNA included in the microbe may be extracted.

The microbe may include various types of microbes. The cell wall may mean external walls of bacteria or molds of the microbes, and the protein shell may mean external walls of viruses of the microbes.

The discharge apparatus 200 may be operated so that the high voltage is applied through the voltage supply unit 210 to destroy the external wall of the microbe. In this case, it may be understood that the applied high voltage is higher than the voltage applied to collect the microbe.

That is, when the high voltage applied to the discharge electrode 220 to collect the microbe is called "voltage 1" and the voltage applied to the discharge electrode 220 to destroy the external wall of the microbe is called "voltage 2", the voltage 2 may form a voltage that is higher than the voltage 1.

Meanwhile, levels of the voltages at which external walls of various microbes can be destroyed may be different from each other. For example, the protein shell of the virus may be destroyed by even a relatively low voltage to extract a DNA, but the cell wall of the bacterium is destroyed when a higher voltage is applied. In addition, the cell wall of the mold may be destroyed when a voltage that is higher than the voltage applied to destroy the cell wall of the bacterium is applied.

During a process of destroying the external wall of the microbe, the level of the voltage applied to the discharge electrode 200 may be changed.

In detail, in the course of measuring the airborne microbe, the levels of the voltages applied to the discharge electrode 200 may be controlled to be sequentially increased and thus destroy the external wall of the weak microbe in advance and then destroy the external wall of the relatively strong microbe.

For example, a voltage (voltage 2-1) enough to destroy the protein shell of the virus may be applied in advance to extract only the DNA of the virus, and the DNA may be passed through a reagent injection apparatus 300 and a light emission measurement apparatus 400 as will be described later to measure only a concentration of the virus of the airborne microbes (first step).

A voltage (voltage 2-2) enough to destroy the cell wall of the bacterium may be then applied to extract the DNA of the bacterium, and the DNA may be passed through the reagent injection apparatus 300 and the light emission measurement apparatus 400 to measure a concentration of the bacterium of the airborne microbes (second step). In this case, since the measured concentration of the microbe may include both the concentration of the virus and the concentration of the bacterium, the concentration of the bacterium may be calculated by subtracting the concentration of the first step from the concentration of the second step.

After the concentration of the bacterium is measured, a voltage (voltage 2-3) enough to destroy the cell wall of the mold may be applied to extract the DNA, and the DNA may be passed through the reagent injection apparatus 300 and the light emission measurement apparatus 400 to measure a concentration of the mold of the airborne microbes (third step). In this case, since the measured concentration of the microbe may include both the concentrations of the virus and the bacterium and the concentration of the mold, the concentration of the mold may be calculated by subtracting the concentration of the second step from the concentration of the third step.

As described above, there is an effect in that the levels of the voltages applied to the discharge electrode 220 are sequentially increased to sequentially destroy the external walls of the viruses, the bacteria, and the molds and thus extract the DNA, thereby sorting and measuring the concentration of the microbe for each type.

The airborne microbial measurement apparatus 10 further includes the reagent injection apparatus 300 injecting a dyeing reagent (fluorescent dye) to the microbe from which the DNA is extracted through the discharge apparatus 200. The reagent injection apparatus 300 may be disposed at a position which is unidirectionally spaced apart from the discharge apparatus 200.

The reagent injection apparatus 300 may be disposed outside the film unit 100 to supply the dyeing reagent to the microbe attached to the film unit 100.

In this case, the film unit 100 can move frontward or rearward. Herein, it is understood that the term "frontward" is a direction which is headed for the reagent injection apparatus 300 from the discharge apparatus 200 and the term "rearward" is a direction which is headed for the discharge apparatus 200 from the reagent injection apparatus 300.

For example, the film unit 100 may be combined with a rotatable roller or a belt movable frontward or rearward to move. In another example, the film unit 100 may be wound around two rollers spaced apart from each other to unlimitedly rotate (caterpillar mode).

In addition, the film unit 100 may be fixed when each process as will be described in FIG. 8 is performed, and move to perform a process of a subsequent step. On the other hand, the film unit 100 may continuously move at a slow rate so that each process is performed for a short time.

When the discharge apparatus 200 is operated to collect the microbe on the surface of the film unit 100 and destroy the external wall of the microbe and thus finish a DNA extraction process, the film unit 100 may move, accordingly, the microbe or the DNA may be positioned at a side of the reagent injection apparatus 300.

When the microbe or the DNA is positioned in a supply region of the reagent injection apparatus 300, the dyeing reagent may be sprayed or injected through the reagent injection apparatus 300 into the microbe or the DNA. The reagent injection apparatus 300 may include a nozzle through which the dyeing reagent is emitted. In addition, it is understood that the supply region is a portion of the region of the film unit 100 and a distribution region of the dyeing reagent emitted through the reagent injection apparatus 300.

When the dyeing reagent is reacted with the DNA, light emission or fluorescence of a predetermined intensity may occur.

The airborne microbial measurement apparatus 10 further includes the light emission measurement apparatus 400 to sense the quantity of emitted light or fluorescent light generated while passing through the reagent injection apparatus 300. The light emission measurement apparatus 400 may be disposed at a position which is unidirectionally spaced apart from the reagent injection apparatus 300.

When supplying of the dyeing reagent is finished, the film unit 100 may move to position the DNA of the microbe subjected to light emission at a side of the light emission measurement apparatus 400, and the light emission measurement apparatus 400 may be operated.

The intensity of light emitted from the DNA may be measured by the light emission measurement apparatus 400, and the concentration or the degree of contamination of the microbe may be calculated through the measured intensity of light or the number of light emission points.

The light emission measurement apparatus 400 may include relatively low-priced LEDs and CCD(Charge-coupled device) cameras. For example, the LED may be a blue LED.

In addition, the light emission measurement apparatus 400 may further include a display unit displaying the measured intensity of light, and the concentration or the degree of contamination of the microbe.

FIG. 4 is a block diagram showing a constitution of the airborne microbial measurement apparatus according to the embodiment.

Referring to FIG. 4, the airborne microbial measurement apparatus 10 according to the embodiment includes the discharge apparatus 200, the reagent injection apparatus 300, and the light emission measurement apparatus 400.

In detail, the discharge apparatus 200 includes the voltage supply unit 210 applying the high voltage, the discharge electrode 220 generating a strong electric field due to the high voltage applied from the voltage supply unit 210, the earth electrode 230 spaced apart from the discharge electrode 220, and a controller 250 controlling the voltage applied from the voltage supply unit 210.

The controller 250 may control the level of the voltage applied from the voltage supply unit 210 in the course of collecting the airborne microbe and destroying the external wall of the collected microbe.

In detail, in order to collect the airborne microbe on the film unit 100 from air, a voltage having the level of the first voltage may be applied from the voltage supply unit 210.

In addition, in order to destroy the external wall of the microbe collected on the film unit 100, a voltage having the level of the second voltage may be applied from the voltage supply unit 210. Herein, the second voltage may be higher than the first voltage.

However, the levels of the voltages at which the external wall is destroyed may be different from each other according to a type of microbe. Accordingly, the controller 250 may control the voltage so that the voltage having the level enough to destroy one or more microbes of various types of microbes is applied.

As described above, the microbe may include the virus, the bacterium, and the mold. In addition, the level of the voltage at which the external wall is destroyed is lowest for the virus (voltage 2-1), and the levels may be sequentially increased for the bacterium (voltage 2-2) and the mold (voltage 2-3).

For example, when the voltage that is the same as or higher than the voltage 2-3 is applied from the voltage supply unit 210, all of the external walls of the virus, the bacterium, and the mold may be destroyed and the DNA of each microbe may be extracted.

In addition, the extracted DNA of each microbe may receive the dyeing reagent while passing through the reagent injection apparatus 300 to emit light or fluorescent light, and the quantity (intensity or the number of light emission points) of emitted light may be sensed while the DNA passes through the light emission measurement apparatus 400. That is, the concentration or the degree of contamination of all the microbes may be calculated.

On the other hand, when the voltage that is the same as or higher than the voltage 2-1 and the same as or lower than the voltage 2-2 is applied from the voltage supply unit 210, the external wall of the virus may be destroyed to extract the DNA but the external walls of the bacterium and the mold may not be destroyed.

Further, when the voltage that is the same as or higher than the voltage 2-2 and the same as or lower than the voltage 2-3 is applied from the voltage supply unit 210, the external walls of the virus and the bacterium may be destroyed to extract the DNA but the external wall of the mold may not be destroyed.

The controller 250 may control the voltage so that the levels of the voltages applied from the voltage supply unit 210 are sequentially increased.

First, the voltage 2-1 is applied from the voltage supply unit 210 to destroy the external wall, that is, the protein shell, of the virus and thus extract the DNA. The extracted DNA passes through the reagent injection apparatus 300 and the light emission measurement apparatus 400, and in this course, the concentration or the degree of contamination of the virus may be calculated.

Then, the film unit 100 may move again to a side of the discharge apparatus 200 (move rearward), and the voltage 2-2 may be applied from the voltage supply unit 210. The external wall, that is, the cell wall, of the bacterium of the collected microbes is destroyed due to the applied voltage to extract the DNA. The extracted DNA passes through the reagent injection apparatus 300 and the light emission measurement apparatus 400, and in this course, the concentration or the degree of contamination of the bacterium may be calculated.

Then, the film unit 100 may move again to a side of the discharge apparatus 200 (move rearward), and the voltage 2-3 may be applied from the voltage supply unit 210. The external wall, that is, the cell wall, of the bacterium of the collected microbes is destroyed due to the applied voltage to extract the DNA. The extracted DNA passes through the reagent injection apparatus 300 and the light emission measurement apparatus 400, and in this course, the concentration or the degree of contamination of the bacterium may be calculated.

FIGS. 5 to 7 are views showing an airborne microbial measurement process according to the embodiment, and FIG. 8 is a flowchart showing an airborne microbial measurement method according to the embodiment.

Referring to FIGS. 5 to 8, when the discharge apparatus 200 is operated to apply the high voltage of the voltage 1 from the voltage supply unit 210, the airborne microbe is collected from air on the surface of the film unit 100 in operation S11.

In addition, when the voltage 2 that is higher than the voltage 1 is applied from the voltage supply unit 210, the external wall of the microbe collected on the surface of the film unit 100 may be destroyed. When the external wall of the microbe is destroyed, the DNA that is present in the microbe may be extracted.

As described above, the external wall of the microbe may include the protein shell of the virus, the cell wall of the bacterium, or the cell wall of the mold in operation S 12.

After the microbe is collected and the cell wall is destroyed, the film unit 100 moves frontward to position the extracted DNA at a side of the reagent injection apparatus 300. In addition, the dyeing reagent is emitted from the reagent injection apparatus 300 to be injected into the microbe or the DNA, and the DNA is reacted with the dyeing reagent to cause light emission or fluorescence of a predetermined intensity in operation S13.

After light emission or fluorescence of the DNA occurs, the film unit 100 moves frontward to position the DNA of light emission or fluorescence at a side of the light emission measurement apparatus 400. In addition, the light emission measurement apparatus 400 may be operated to sense the quantity of emitted light or fluorescent light, and the concentration of the microbe according to the sensed quantity of light may be calculated by using a computer program.

As described above, there is an effect in that since the constitution of the airborne microbial measurement apparatus and the measurement method thereof according to the embodiment are simple, a cost is low.

Meanwhile, as described above, when various types of microbes are collected on the film unit 100, the levels of the voltages applied from the voltage supply unit 210 can be sequentially increased to selectively destroy the external walls of the microbes and thus extract the DNAs. In addition, only the concentration of the corresponding microbe having the extracted DNA can be measured.

Accordingly, among the collected various airborne microbes, the microbe to be measured can be sorted and the concentration thereof can be selectively sensed, and thus easy of use can be increased.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

The invention claimed is:

1. An airborne microbial measurement apparatus comprising:
   a discharge apparatus including a discharge electrode, a voltage supply unit applying a high voltage to the discharge electrode, and a controller controlling the voltage supply unit;
   a substrate provided to a side of the discharge apparatus to collect an airborne microbe from air by the high voltage applied to the discharge electrode, the airborne microbe including viruses, bacteria, and molds;
   a reagent injection apparatus supplying a dyeing reagent to the microbe collected on the substrate or a DNA of the microbe; and
   a light emission measurement apparatus sensing a quantity of light generated from the microbe or the DNA to which the dyeing reagent is supplied,
   wherein:
   the voltage supply unit is configured to apply a variable voltage to the discharge electrode,
   the controller controls the voltage supply unit such that voltage 1 is applied to collect the airborne microbe from air on the substrate, and when the microbe is collected on the substrate, the controller controls the voltage supply unit such that voltage 2, which is higher than the voltage 1, is applied to destroy the external wall of the collected microbe and extract the DNA,
   the controller controls the voltage supply unit such that the level of the voltage 2 is sequentially increased according to a type of the microbe, and
   the controller sequentially calculates concentration of the viruses, bacteria, and molds in order when the extracted DNA of the viruses, bacteria, and molds passes through the reagent injection apparatus and the light emission measurement apparatus.

2. The airborne microbial measurement apparatus according to claim 1, wherein the airborne microbe includes viruses, bacteria, and molds, and the controller controls the voltage supply unit so that the level of the voltage 2 is increased to sequentially destroy protein shells of the viruses, cell walls of the bacteria, and cell walls of the molds.

3. The airborne microbial measurement apparatus according to claim 1, wherein the substrate includes a plastic material having polyethylene and polypropylene mixed therein.

4. The airborne microbial measurement apparatus according to claim 1, wherein the light emission measurement apparatus includes a blue LED and a CCD camera.

5. An airborne microbial measurement method comprising;
   providing the apparatus of claim 1;
   collecting an airborne microbe on the substrate by applying the voltage to a discharge apparatus;
   destroying an external wall of the microbe collected on the substrate and extracting a DNA by applying a voltage to the discharge apparatus;
   injecting a dyeing reagent to the extracted DNA to perform light emission or fluorescence;
   and sensing a quantity of emitted or fluorescent light by using a light emission measurement apparatus
   wherein the collecting of the airborne microbe on the substrate includes applying voltage 1 to the discharge apparatus, and the destroying of the external wall of the microbe collected on the substrate and the extracting of the DNA include applying voltage 2 to the discharge apparatus, and
   wherein the destroying of the external wall of the microbe collected on the substrate and the extracting of the DNA include sequentially increasing the voltage 2 to sequentially destroy external walls of a plurality of microbes from the microbe having a weak external wall to the microbe having a strong externa wall.

* * * * *